US00PP27233P3

(12) United States Plant Patent
Schoone

(10) Patent No.: US PP27,233 P3
(45) Date of Patent: Oct. 4, 2016

(54) ***PHALAENOPSIS* ORCHID PLANT NAMED 'BRIGHT SMILE'**

(50) Latin Name: *Phalaenopsis hybrida*
Varietal Denomination: Bright Smile

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 14/545,294

(22) Filed: Apr. 20, 2015

(65) Prior Publication Data

US 2015/0313056 P1 Oct. 29, 2015

Related U.S. Application Data

(60) Provisional application No. 61/983,605, filed on Apr. 24, 2014.

(30) Foreign Application Priority Data

Apr. 29, 2014 (NL) ..... PBR OPS1093

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Jun. 11, 2016. p. 1.*

* cited by examiner

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Bright Smile' particularly characterized by flowers which are white with some yellow and red/purple in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Bright Smile'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Bright Smile'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Bright Smile' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Bright Smile' originated from a cross made by the inventor in 2001 in Strengweg, Heemskerk, The Netherlands. The female or seed parent is the *Phalaenopsis* cultivar designated '(Spring Song×Key Largo)', unpatented. The male or pollen parent is the *Phalaenopsis* cultivar designated 'Hawaiian Dream', unpatented. The new *Phalaenopsis* 'Bright Smile' was discovered and selected by the inventor as a single flowering plant within the progeny of the stated cross in a controlled environment in 2009 in Strengweg, Heemskerk, The Netherlands.

Asexual reproduction of the new *Phalaenopsis* cultivar by tissue culture (mericloning) was first performed in November, 2009 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Bright Smile', which in combination distinguish this *Phalaenopsis* as a new and distinct cultivar:

1. flowers which are white with some yellow and red/purple in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Bright Smile', the flowers of the female parent '(Spring Song×Key Largo)' are about 11 cm in size, the flowers of the male parent 'Hawaiian Dream' are about 10 cm in size, whereas the flowers of 'Bright Smile' are about 95 cm in size.

Presently, the commercial cultivar to which 'Bright Smile' can be meaningfully compared is 'Snowdance' (unpatented). The petals of 'Bright Smile' are more broadly ovate and the cirrhi of 'Bright Smile' are longer than the cirrhi of 'Snowdance'. The labellum of 'Snowdance' has more red/purple than the labellum of 'Bright Smile'.

BRIEF DESCRIPTION OF THE PHOTOGRAPHS

The accompanying photographs illustrate the overall appearance of the new *Phalaenopsis* 'Bright Smile' showing the colors as true as is reasonably possible with colored reproductions of this type. Colors in the photographs may differ slightly from the color values cited in the detailed botanical description, which accurately describe the color of 'Bright Smile'.

DETAILED BOTANICAL DESCRIPTION

Figure 1:
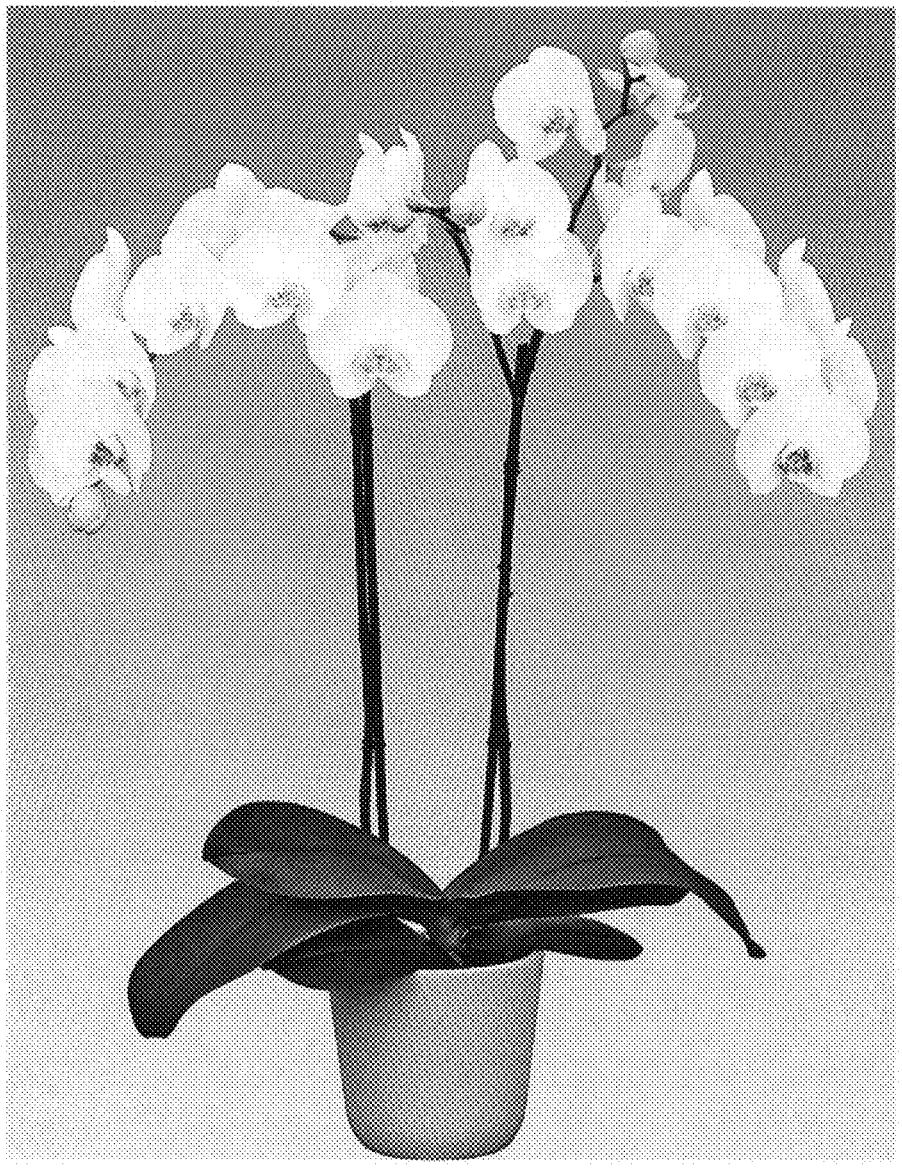
FIG. 1 shows a side view perspective of a typical flowering plant of 'Bright Smile' in a 12 cm pot, at 16 months of age.

The new *Phalaenopsis* cultivar 'Bright Smile' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Bright Smile' as grown in a greenhouse in Strengweg, Heemskerk, The Netherlands, under conditions which closely approximate those generally used in commercial practice. Initially, the ideal temperature to grow plants of 'Bright Smile' is 27° C. during the day and at night. Then, during the flowering phase of 'Bright Smile', the ideal growing temperature is 20-22° C. during the day and 18° C. at night. Light levels for growing 'Bright Smile' are a minimum of 5,000 lux and a maximum of 10,000 lux. A balanced fertilizer with level of 200 ppm N, 87 ppm P, 168 ppm K is applied. Duration of growth of 'Bright Smile' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Bright Smile' plants described is 12 months after potting.

Classification:

*Botanical.—Phalaenopsis hybrida.*

Parentage:

*Female or seed parent.—Phalaenopsis* cultivar designated '(Spring Song×Key Largo)', unpatented.

*Male or pollen parent.—Phalaenopsis* cultivar designated 'Hawaiian Dream', unpatented.

Propagation:

*Type.*—Tissue culture.

*Rooting habit and description.*—Fleshy; approximately 2 mm-6 mm wide and greyed/green in color (RHS 190A); freely branching. It takes 12 weeks for plants growing in tissue culture to initiate roots.

Plant:

*Size at maturity.*—Height (from bottom of pot to highest flower): about 60 cm. Spread: about 50 cm.

*Growth habit.*—Standard; green leaves (RHS 137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19 ° C. about 1-2 racemes with flowers appear.

Foliage:

*Quantity per plant.*—About 6 -8 leaves are produced before flowering.

*Arrangement and attachment.*—Half up/horizontal and on two sides.

*Overall shape of leaf.*—Oval; the tip is blunt and asymmetric.

*Texture (upper & underside).*—Smooth and leathery.

*Pubescence.*—None.

*Mature leaf length.*—About 28 cm.

*Mature leaf width.*—About 10 cm.

*Mature leaf thickness.*—About 2 mm.

*Mature leaf color.*—Upper side: green (RHS 137A). Under side: yellow/green (RHS 146B).

*Leaf base.*—Acute.

*Margin.*—Entire.

*Venation.*—Pattern: parallel. Color of midvein: upper side: green (RHS 137A). Under side: green (RHS 138B).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 2.

*Number of flowers per raceme.*—About 5-16.

*Length.*—About 60 cm.

Peduncle:

*Diameter.*—About 4 mm.

*Strength.*—Strong.

*Aspect.*—Upright.

*Texture*.—Glabrous and smooth.

*Color*.—Brown (RHS N200A) with yellow/green (RHS 146A).

Buds:

*Height* (*from base to tip*).—About 25 mm.

*Diameter* (*at midpoint*).—About 15 mm.

*Shape*.—Oval/egg-shaped.

*Color*.—Yellow/green (RHS 145B).

*Orientation*.—Same as flowers (forward facing).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
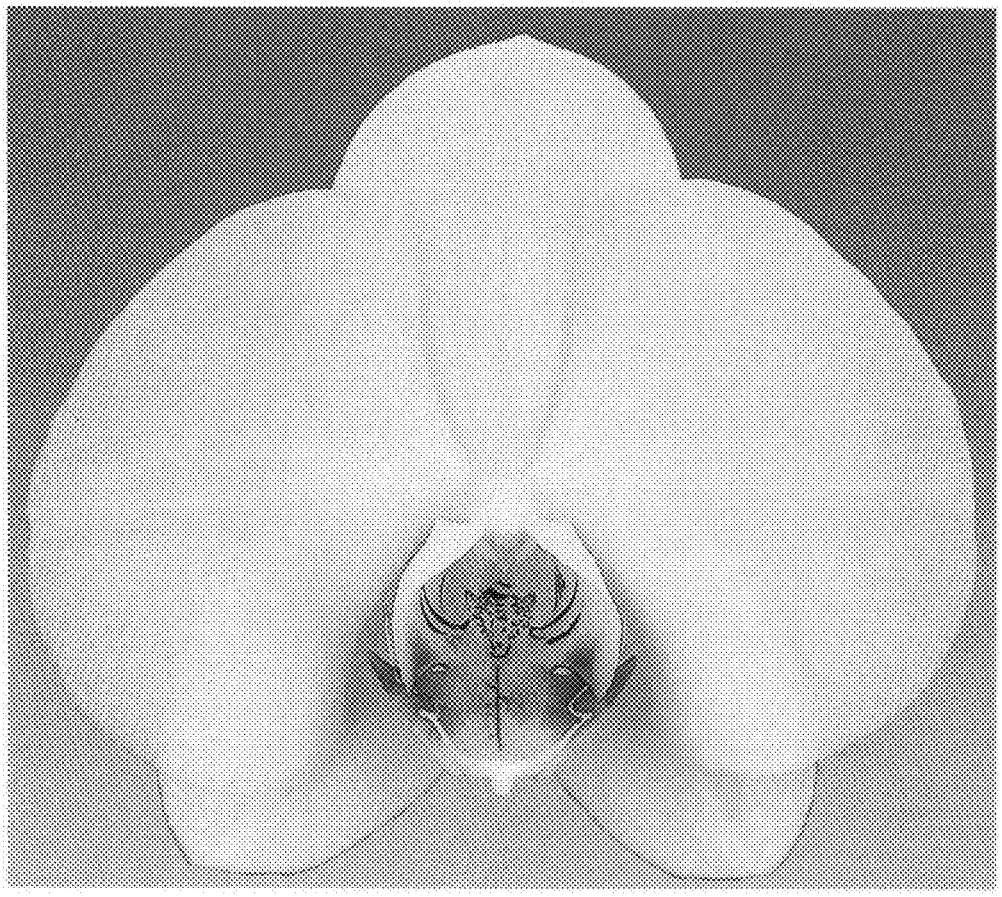
FIG. 2 shows a close-up view of the typical flower of 'Bright Smile'.
Figure 3:
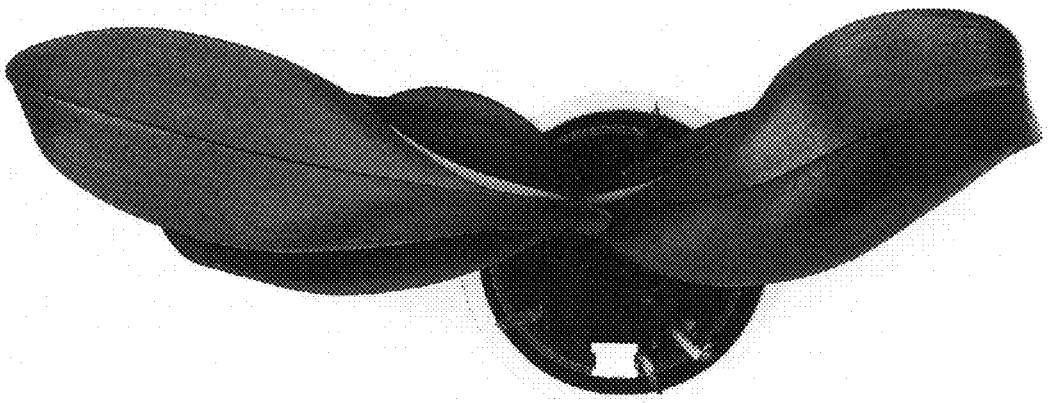
FIG. 3 shows a close-up view of the typical leaves of 'Bright Smile'.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 75 mm. Diameter: about 95 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: oval. Margin: entire and weakly undulate. Base: broadly ovate. Length: about 50 mm. Width: about 40 mm. Texture: Upper surface: smooth and satiny. Under surface: smooth and satiny. Color (when fully opened): upper side: white (RHS NN155C). Under side: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 19 mm. Width (not flattened): about 25 mm. Depth of tube created by lateral lobes of labellum: about 17 mm. Texture: Upper & under surface: smooth and satiny. Color (when fully opened): Mid lobe, upper side: main color is white (RHS NN155C). In the center yellow (RHS 5C) with red/purple (RHS 71A) on the mid vein. On the sides yellow/green (RHS 151 D) with some vague red/purple (RHS 71B) and red/purple (RHS 71D). Under side: main color is white (RHS NN155C). Corners are yellow/green (RHS 155D). Thin edges at the base are red/purple (RHS 71A). Lateral lobes, upper side: main color is white (RHS NN155C). At the lower edges first thin red/purple line (RHS 71A) than yellow/green (RHS 151D). From the base some red/purple stripes (RHS 71A). Under side: white (RHS NN155C) with at the lower edges some yellow/green (RHS 151 C) and a thin red/purple line (RHS 70A). Cirrhi: about 18 mm. Color: white (RHS NN155C) with yellow/green (RHS 150D) en red/purple spots (RHS 71A). Pestle (Callosities): Length: about 7 mm. Width (not flattened): about 7 mm. Color: main color is white (RHS NN155C). On top and on the sides yellow (RHS 8A) and red/purple spots (RHS 71A).

*Sepals*.—Arrangement: Outer whorl comprises 3 sepals, one dorsal and two lateral sepals. Overall shape: elliptical and weakly cupped. Margin: entire and weakly undulate. Length: about 40 mm. Width: about 35 mm. Apex: oval and little pointy. Texture: Upper and under surface: smooth and satiny. Color (when fully opened): Upper side, dorsal: white (RHS NN155C). Lateral: white (RHS NN155C). At the base some yellow/green (RHS 150C) with red/purple spots (RHS 70B). Under side, dorsal & lateral: white (RHS NN155C) with a yellow/green (RHS 150C) haze.

*Pedicel*.—Length: about 35 mm. Diameter: about 3 mm. Texture: glabrous and smooth. Color: starting at the flower yellow/green (RHS 150D) which runs into yellow/green (RHS 149B) and then yellow/green (RHS 144A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: white (RHS NN155C).

*Pollinia*.—Quantity: two. Diameter: about 2 mm. Color: yellow/orange (RHS 17A).

*Ovary*.—Length: about 3 mm. Diameter: about 4 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Bright Smile', as illustrated and described herein.

* * * * *